US008617585B2

(12) United States Patent
Boden et al.

(10) Patent No.: US 8,617,585 B2
(45) Date of Patent: Dec. 31, 2013

(54) INTRAMEDULLARY DRUG DELIVERY DEVICE AND METHOD OF TREATING BONE FRACTURES

(75) Inventors: Scott D. Boden, Atlanta, GA (US); Jeffrey L. Scifert, Arlington, TN (US); James S. Marotta, Memphis, TN (US)

(73) Assignee: Warsaw Orthopedic, Inc., Warsaw, IN (US)

( * ) Notice: Subject to any disclaimer, the term of this patent is extended or adjusted under 35 U.S.C. 154(b) by 1822 days.

(21) Appl. No.: 11/388,250

(22) Filed: Mar. 23, 2006

(65) Prior Publication Data

US 2007/0225219 A1   Sep. 27, 2007

(51) Int. Cl.
*A61F 2/00*   (2006.01)
(52) U.S. Cl.
USPC ............... 424/423; 514/16.7; 604/101.03; 604/101.05; 606/53; 606/255; 606/62
(58) Field of Classification Search
USPC .................................................. 604/101.03
See application file for complete search history.

(56) References Cited

U.S. PATENT DOCUMENTS

| | | | |
|---|---|---|---|
| 5,423,850 A * | 6/1995 | Berger | 606/192 |
| 5,514,137 A | 5/1996 | Coutts | |
| 5,549,625 A * | 8/1996 | Bircoll | 606/192 |
| 5,681,289 A | 10/1997 | Wilcox et al. | |
| 6,387,098 B1 | 5/2002 | Cole et al. | |
| 2002/0177866 A1 | 11/2002 | Weikel et al. | |
| 2004/0068226 A1 | 4/2004 | Brannon | |
| 2004/0098015 A1 | 5/2004 | Weikel et al. | |
| 2004/0153090 A1 | 8/2004 | Vandewalle | |
| 2005/0015060 A1 | 1/2005 | Sweeney | |
| 2005/0209629 A1 | 9/2005 | Kerr et al. | |
| 2005/0220771 A1 * | 10/2005 | Deslauriers et al. | 424/93.7 |
| 2006/0013851 A1 | 1/2006 | Giroux | |

* cited by examiner

*Primary Examiner* — Hasan Ahmed
(74) *Attorney, Agent, or Firm* — Sorell Lenna & Schmidt LLP

(57) ABSTRACT

An intramedullary drug delivery device is disclosed and can be inserted within a bone canal of a bone. The intramedullary drug delivery device can include a housing. A drug delivery region can be established along the housing. Also, the drug delivery region can be configured to substantially span a fracture within the bone.

26 Claims, 11 Drawing Sheets

US 8,617,585 B2

INTRAMEDULLARY DRUG DELIVERY DEVICE AND METHOD OF TREATING BONE FRACTURES

FIELD OF THE DISCLOSURE

The present disclosure relates generally to orthopedics and orthopedic surgery. More specifically, the present disclosure relates to devices used to deliver drugs within bones.

BACKGROUND

An adult human skeleton includes two hundred and six bones. During a lifetime a human may fracture one or more of these bones. Some fractures may be treated using a casting process. Certain other fractures of long bones may be treated using an intramedullary rod. For example, fractures of the ulnae, radii, humeri, femora, tibiae, and fibulae can be treated using an intramedullary rod. In such cases, the intramedullary rod can be permanently installed within these bones and the bone can be allowed to heal around the intramedullary rod. It can be advantageous to deliver a therapeutic agent to an area surrounding a fracture prior to the installation of the intramedullary rod.

DETAILED DESCRIPTION OF THE DRAWINGS

Figure 1:
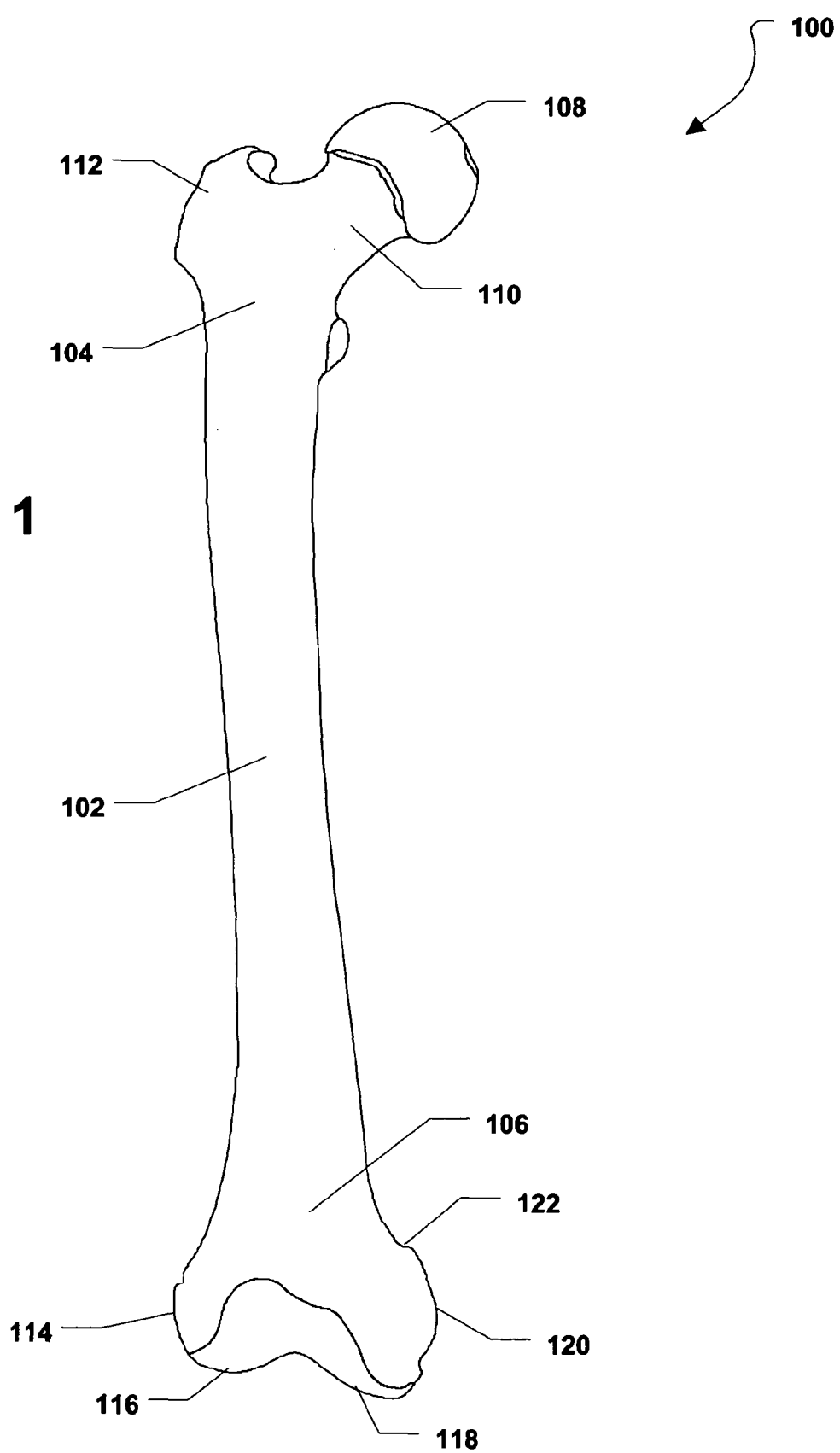
FIG. 1 is a plan view of a femur.

An intramedullary drug delivery device is disclosed and can be inserted within a bone canal of a bone. The intramedullary drug delivery device can include a housing. A drug delivery region can be established along the housing. Also, the drug delivery region can be configured to substantially span a fracture within the bone.

In another embodiment, a method of treating a bone fracture is disclosed and can include inserting an intramedullary drug delivery device within a bone such that a drug delivery region of the intramedullary drug delivery device straddles the fracture. The method can also include delivering a therapeutic agent in an area surrounding the fracture.

In yet another embodiment, a method of treating a bone fracture is disclosed and includes inserting an intramedullary drug delivery device within a bone such that a drug delivery region of the intramedullary drug delivery device straddles the fracture. Further, the method can include inflating a first balloon and a second balloon adjacent to the drug delivery region. The method can also include delivering a therapeutic agent in an area surrounding the fracture.

In still another embodiment, an intramedullary drug delivery device is disclosed and can be inserted within a bone canal of a bone. The intramedullary drug delivery device can include a housing. A first radiopaque marker can be on the housing. Further, a second radiopaque marker can be on the housing and can be distanced from the first radiopaque marker. A drug delivery region can be established along the housing between the first radiopaque marker and the second radiopaque marker. Moreover, the intramedullary drug delivery device can include a drug delivery fenestration that can be established in the housing within the drug delivery region.

In yet still another embodiment, an intramedullary drug delivery device is disclosed and can be inserted within a bone canal of a bone. The intramedullary drug delivery device can include a housing. A first radiopaque marker can be on the housing. A second radiopaque marker can be on the housing and can be distanced from the first radiopaque marker. Further, a drug delivery region can be established along the housing between the first radiopaque marker and the second radiopaque marker. The intramedullary drug delivery can also include a first balloon adjacent to the drug delivery region and a second balloon adjacent to the drug delivery region.

In another embodiment, an intramedullary drug delivery device is disclosed and can be inserted within a bone canal of a bone. The intramedullary drug delivery device can include a drug delivery region that can substantially span a fracture within the bone. Also, the intramedullary drug delivery device can include a therapeutic agent that can be deliverable to an area substantially near the fracture via the drug delivery region.

In yet another embodiment, a kit for treating a fracture within a bone is disclosed and can include an intramedullary drug delivery device that can be inserted within the bone. The intramedullary drug delivery device can include a drug delivery region that can substantially span the fracture. The kit can also include a therapeutic agent that can be deliverable to an area within the bone substantially near the fracture via the drug delivery region. Additionally, the kit can include an intramedullary rod that can be installed within the bone.

Description of Relevant Anatomy

Referring to FIG. 1, a femur is shown and is generally designated 100. As shown, the femur 100 includes a femoral body 102 that can define a proximal end 104 and a distal end 106. Further, the femur 100 can include a femoral head 108 that extends from the proximal end 104 of the femoral body 102. Further, a neck 110 can be established between the femoral head 108 and the femoral body 102. In a particular embodiment, the femoral head 108 can fit into a hip socket, a.k.a., an acetabulum (not shown).

As further illustrated in FIG. 1, the proximal end 104 of the femoral body 102 can include a greater trochanter 112 adjacent to the neck 106. Additionally, the distal end 106 of the femoral body 102 can include a lateral epicondyle 114, a lateral condyle 116, a medial condyle 118, and a medial epicondyle 120. In a particular embodiment, the lateral condyle 116 and the medial condyle 118 can articulate with a patella (not shown). FIG. 1 also indicates that the femur 100 can include an adductor tubercle 122.

Description of a First Embodiment of an Intramedullary Drug Delivery Device

Figure 2:
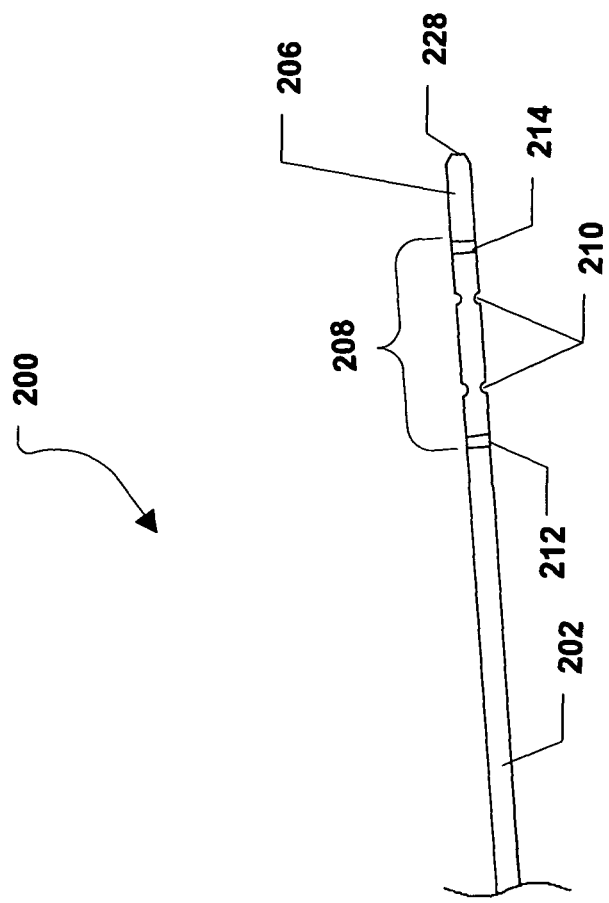
FIG. 2 is a plan view of an intramedullary drug delivery device.
Figure 2:
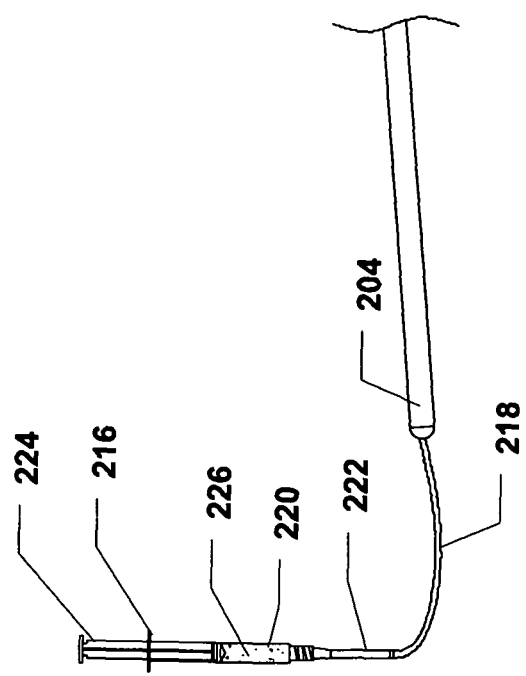

Referring to FIG. 2, a first embodiment of an intramedullary drug delivery device is shown and is generally designated

200. As shown, the intramedullary drug delivery device 200 can include a housing 202 having a proximal end 204 and a distal end 206. In a particular embodiment, the housing 202 can be generally elongated. Further, the housing 202 can be hollow and can include a cross-section that can be generally circular. In one or more alternative embodiments, the cross-section of the housing 202 can be generally circular, generally rectangular, generally square, generally triangular, generally trapezoidal, generally rhombic, generally quadrilateral, any generally polygonal shape, or any combination thereof.

In a particular embodiment, the intramedullary drug delivery device 200 can include a drug delivery region 208 adjacent to the distal end 206 of the intramedullary drug delivery device 200. The drug delivery region 208 can include one or more drug delivery fenestrations 210 through which one or more therapeutic agents can be expelled from the inrtraedullary drug delivery device 200. In a particular embodiment, the therapeutic agents can be bone morphogenetic protein (BMP), demineralized bone matrix (DBM), cellular material, platelet gel, or a combination thereof. Further, the therapeutic agents can include a cement, a putty, or a combination thereof, which can provide a scaffold for passive bone formation in addition to acting as a carrier for another therapeutic agent, e.g., one or more of the therapeutic agents described above.

As shown in FIG. 2, the drug delivery region 208 of the intramedullary drug delivery device 200 can be established between a first radiopaque marker 212 and a second radiopaque marker 214. Further, the drug delivery fenestrations 210 can be established between the radiopaque markers 212, 214.

FIG. 2 further shows that a drug delivery syringe 216 can be connected to the housing 202 via a drug delivery tube 218. In a particular embodiment, the drug delivery tube 218 can extend through the proximal end 204 of the housing 202 and can lead to the drug delivery region 208 of the intramedullary drug delivery device 200. The drug delivery syringe 216 can include a syringe housing 220. The syringe housing 220 can include a tip 222 and the drug delivery tube 218 can be coupled, or otherwise connected to the tip 222 of the syringe housing 220. Further, a plunger 224 can be inserted within the syringe housing 220. In alternative embodiments, the drug delivery syringe 216 can be removably or substantially permanently connected to the drug deliver tube 218, which can be removably or substantially permanently connected to the housing 202.

Figure 3:
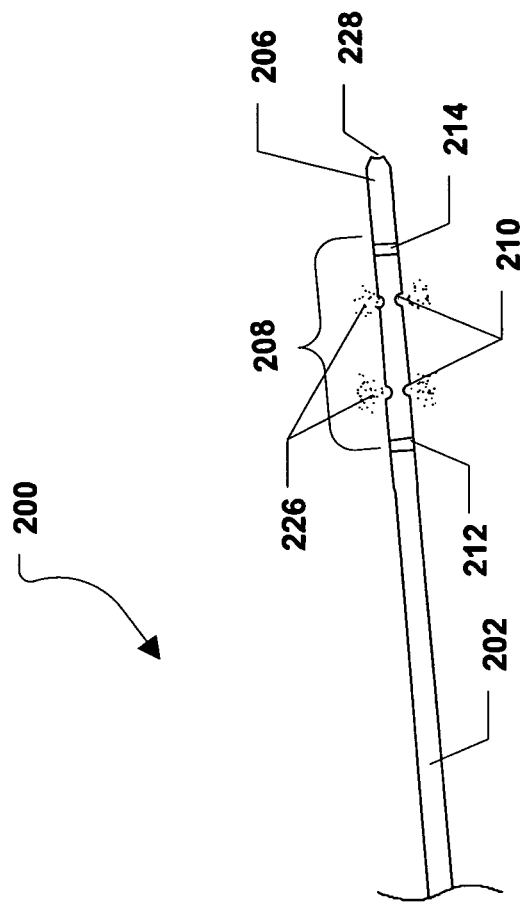
FIG. 3 is another plan view of an intramedullary drug delivery device.
Figure 3:
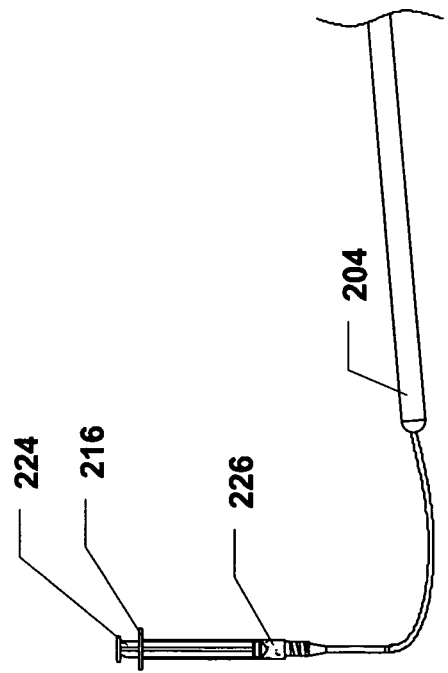

In a particular embodiment, when the plunger 224 of the drug delivery syringe 216 is depressed, as shown in FIG. 3, a therapeutic agent 226 can be delivered from the drug delivery syringe 216 to the drug delivery region 208 of the intramedullary drug delivery device 200 via the drug delivery tube 218. The therapeutic agent 226 can be expelled from the intramedullary drug delivery device 200 via the drug delivery fenestrations 210 within drug delivery region 208. In a particular embodiment, the therapeutic agent 226 can be one or more of the therapeutic agents described herein.

FIG. 2 further shows that the distal end 206 of the intramedullary drug delivery device 200 can include a guide wire hole 228 that can lead to a lumen (not shown) formed within the intramedullary drug delivery device 200. As such, the intramedullary drug delivery device 200 can be inserted over a guide wire (not shown) or a guide pin (not shown). The guide wire can facilitate insertion of the intramedullary drug delivery device 200.

Figure 4:
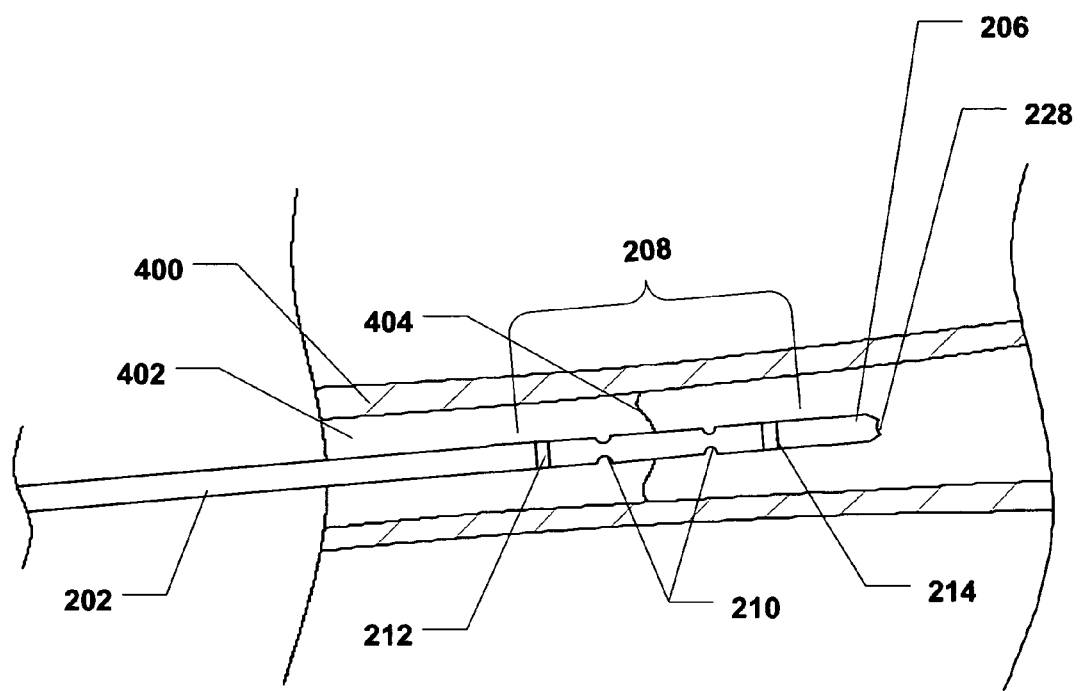
FIG. 4 is a plan view of the intramedullary drug delivery device within a bone.

During use, the intramedullary drug delivery device 200 can be placed within a bone 400, as depicted in FIG. 4. In a particular embodiment, the intramedullary drug delivery device 200 can be inserted within a bone canal 402 of the bone 400. In a particular embodiment, the bone 400 can be an ulna, a radius, a humerus, a femur, a tibia, a fibula, or any other similar bone. The radiopaque markers 212, 214 can be used to properly locate the drug delivery region 208 of the intramedullary drug delivery device 200 at or near a fracture 404 within the bone 400. Specifically, in the presence of X-rays, e.g., from a fluoroscopy device, the radiopaque markers 212, 214 will be visible to allow placement of the intramedullary drug delivery device 200. In a particular embodiment, the intramedullary drug delivery device 200 can be placed so that the drug delivery region 208 spans, or otherwise straddles, the fracture 404 within the bone 400.

Figure 5:
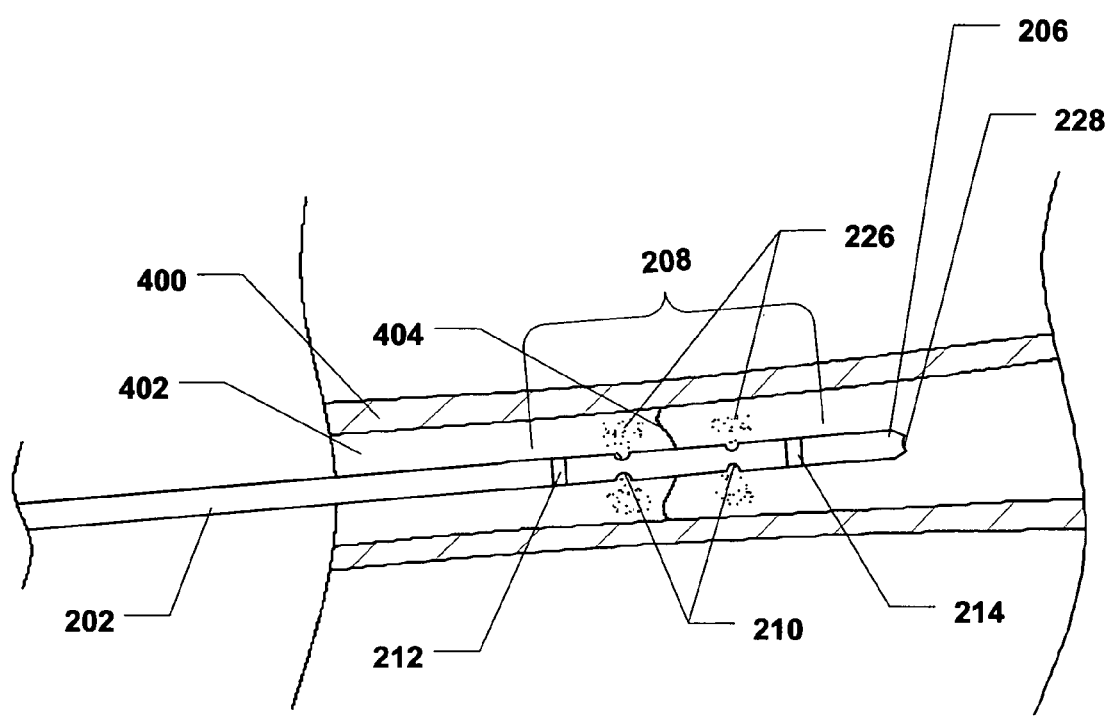
FIG. 5 is another plan view of the intramedullary drug delivery device within a bone.

Further, when the plunger 224 of the drug delivery syringe 216 is depressed, a therapeutic agent 226 can be delivered from the intramedullary drug delivery device 200 to the area substantially near or adjacent to the fracture 404, as shown in FIG. 5.

Description of a First Method of Treating a Bone Fracture

Figure 6:
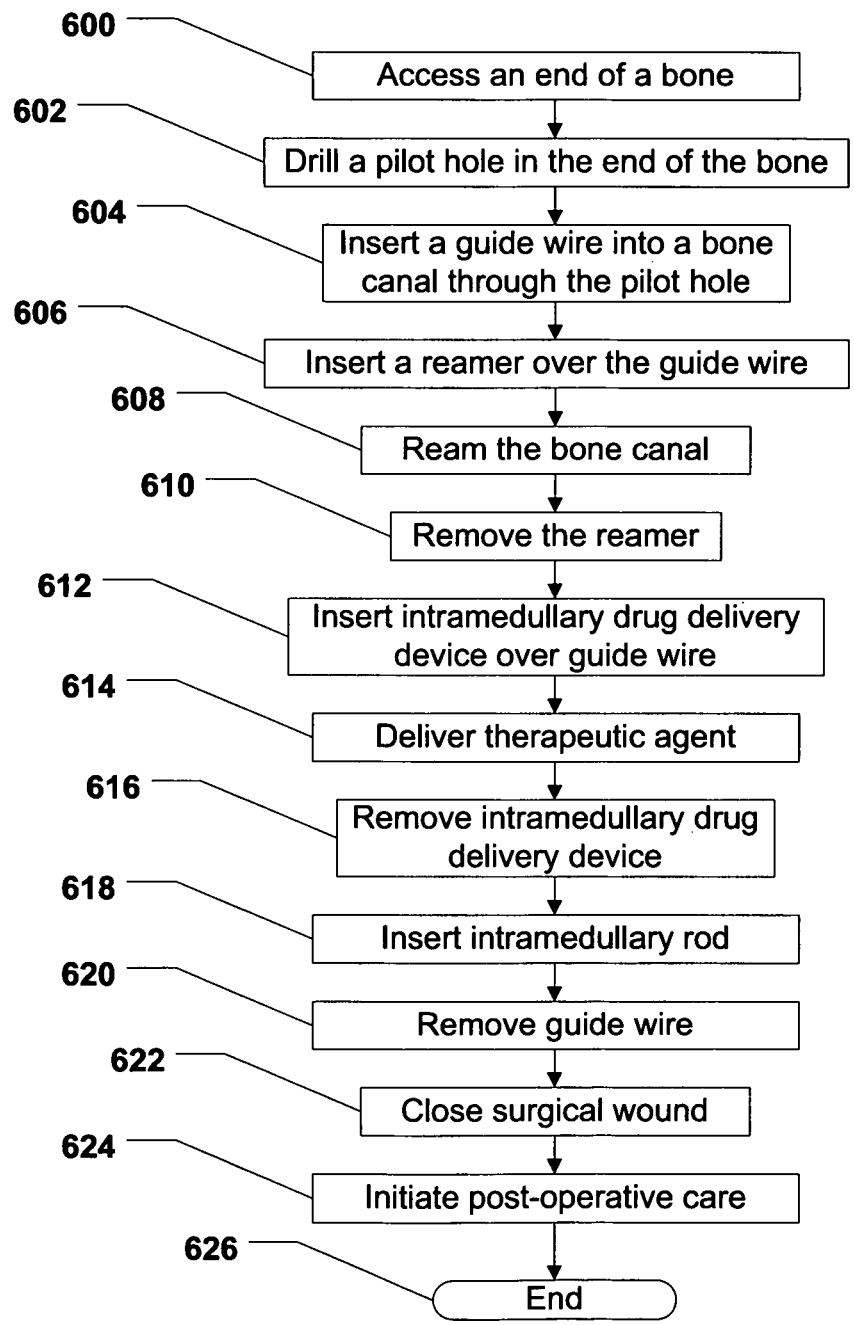
FIG. 6 is a flow chart of a first method of treating a bone fracture.

Referring to FIG. 6, a first method of treating a bone fracture is shown and commences at block 600. At block 600, an end of a bone can be accessed. At block 602, a pilot hole can be drilled in the end of the bone. Moving to block 604, a guide wire, or guide pin, can be inserted into a bone canal within the bone through the pilot hole. Thereafter, at block 606, a bone reamer can be inserted into the bone canal over the guide wire.

Proceeding to block 608, the bone canal can be reamed using the bone reamer. At block 610, the bone reamer can be removed from the bone canal. Moving to block 612, an intramedullary drug delivery device can be inserted over the guide wire. In a particular embodiment, the intramedullary drug delivery device can be an intramedullary drug delivery device according to one or more of the embodiments described herein. Further, in a particular embodiment, the intramedullary drug delivery device can be positioned within the bone so that a drug delivery region of the intramedullary drug delivery device straddles a fracture in the bone. One or more radiopaque markers on the intramedullary drug delivery device, in conjunction with an X-ray device or a fluoroscopy device, can facilitate the positioning of the intramedullary drug delivery device within the bone.

Continuing to block 614, a therapeutic agent can be delivered to the bone canal. In a particular embodiment, the therapeutic agent can be delivered to the area immediately around the fracture. Also, in a particular embodiment, the therapeutic agent can be delivered to the bone canal by depressing a plunger on a syringe of the intramedullary drug delivery device. Further, in a particular embodiment, the therapeutic agent can be bone morphogenetic protein (BMP), demineralized bone matrix (DBM), cellular material, platelet gel, or a combination thereof. Also, the therapeutic agents can include a cement, a putty, or a combination thereof, which can provide a scaffold for passive bone formation in addition to acting as a carrier for another therapeutic agent, e.g., one or more of the therapeutic agents described above.

At block 616, the intramedullary drug delivery device can be removed from the bone canal. Thereafter, at block 618, an intramedullary rod can be inserted into the bone canal over the guide wire. At block 620, the guide wire can be removed. Moving to block 622, the surgical wound, e.g., the surgical wound used to access the end of the bone, can be closed. The surgical wound can be closed by simply allowing the patient's skin to close due to the elasticity of the skin. Alternatively, the surgical wound can be closed using sutures, surgical staples, or any other surgical technique well known in the art. At block 624, postoperative care can be initiated. Then, the method can end at state 626.

Description of a Second Embodiment of an Intramedullary Drug Delivery Device

Figure 7:
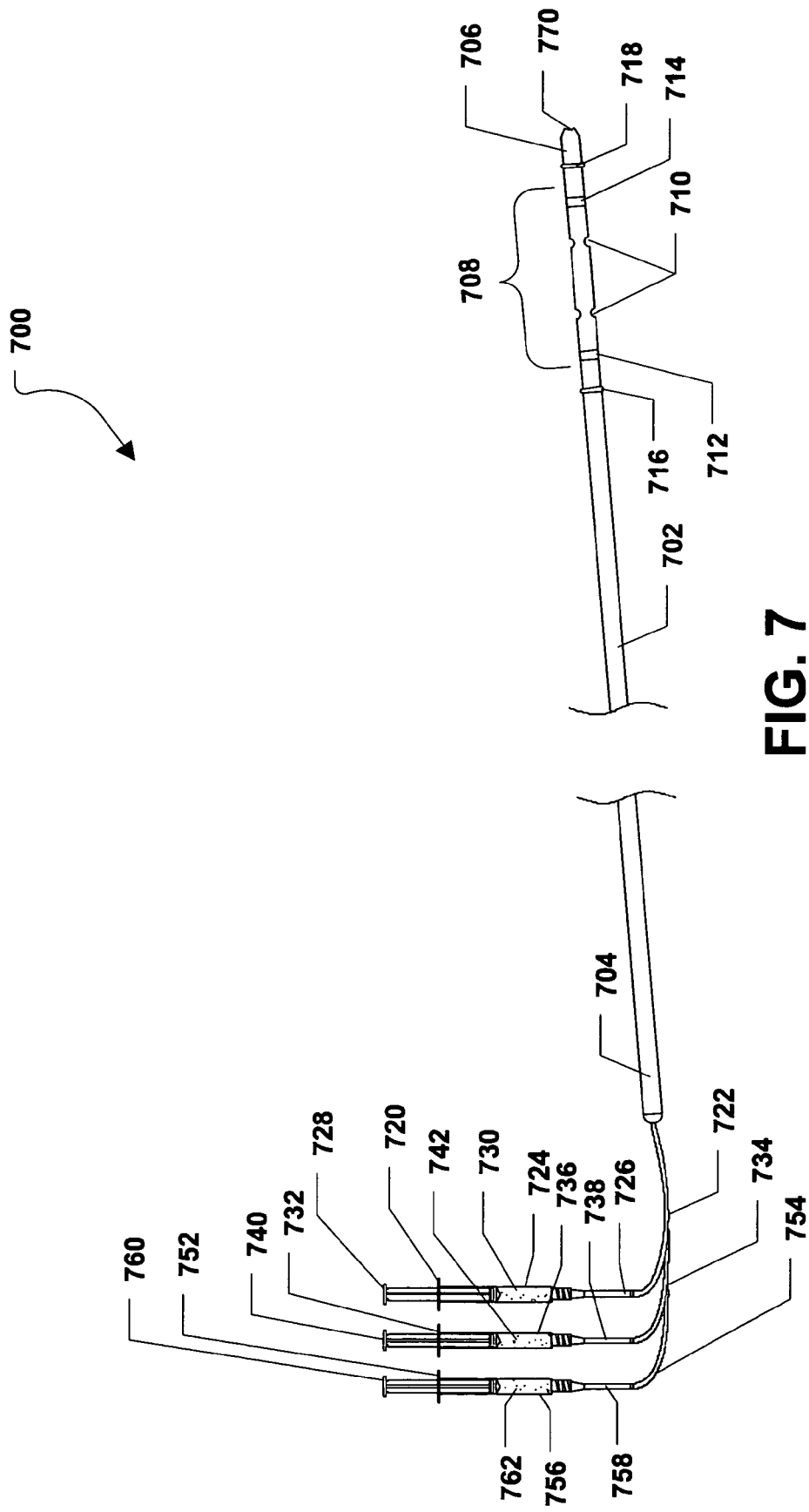
FIG. 7 is a plan view of a second embodiment of an intramedullary drug delivery device.

Referring to FIG. 7, a second embodiment of an intramedullary drug delivery device is shown and is generally designated 700. As shown, the intramedullary drug delivery device 700 can include a housing 702 having a proximal end 704 and a distal end 706. In a particular embodiment, the housing 702 can be generally elongated. Further, the housing 702 can be hollow and can include a cross-section that can be generally circular. In one or more alternative embodiments, the cross-section of the housing 702 can be generally circular, generally rectangular, generally square, generally triangular, generally trapezoidal, generally rhombic, generally quadrilateral, any generally polygonal shape, or any combination thereof.

In a particular embodiment, the intramedullary drug delivery device 700 can include a drug delivery region 708 adjacent to the distal end 706 of the intramedullary drug delivery device 700. The drug delivery region 708 can include one or more drug delivery fenestrations 710 through which one or more therapeutic agents can be expelled from the intramedullary drug delivery device 700. In a particular embodiment, the therapeutic agents can be bone morphogenetic protein (BMP), demineralized bone matrix (DBM), cellular material, platelet gel, or a combination thereof. Further, the therapeutic agents can include a cement, a putty, or a combination thereof, which can provide a scaffold for passive bone formation in addition to acting as a carrier for another therapeutic agent, e.g., one or more of the therapeutic agents described above.

As shown in FIG. 7, the drug delivery region 708 of the intramedullary drug delivery device 700 can be established between a first radiopaque marker 712 and a second radiopaque marker 714. Further, the drug delivery fenestrations 710 can be established between the radiopaque markers 712, 714.

FIG. 7 further indicates that the intramedullary drug delivery device 700 can include a first balloon 716 adjacent to the drug delivery region 708 between the drug delivery region 708 and the proximal end 704 of the housing 702. Also, the intramedullary drug delivery device 700 can include a second balloon 718 between the drug delivery region 708 and the distal end 706 of the housing 702. Each balloon 716, 718 can be moved between a deflated position, shown in FIG. 7, and an inflated position, shown in FIG. 8. In a particular embodiment, the first balloon 716 can be disposed over the first radiopaque marker 712 and the second balloon 718 can be disposed over the second radiopaque marker 714. In an alternative embodiment, the balloons 716, 718 can be radiopaque.

FIG. 7 further shows that a drug delivery syringe 720 can be connected to the housing 702 via a drug delivery tube 722. In a particular embodiment, the drug delivery tube 722 can extend through the proximal end 704 of the housing 702 and can lead to the drug delivery region 708 of the intramedullary drug delivery device 700. The drug delivery syringe 720 can include a syringe housing 724. The syringe housing 724 can include a tip 726 and the drug delivery tube 722 can be coupled, or otherwise connected to the tip 726 of the syringe housing 724. Further, a plunger 728 can be inserted within the syringe housing 724. In alternative embodiments, the drug delivery syringe 720 can be removably or substantially permanently connected to the drug deliver tube 722, which can be removably or substantially permanently connected to the housing 702.

Figure 8:
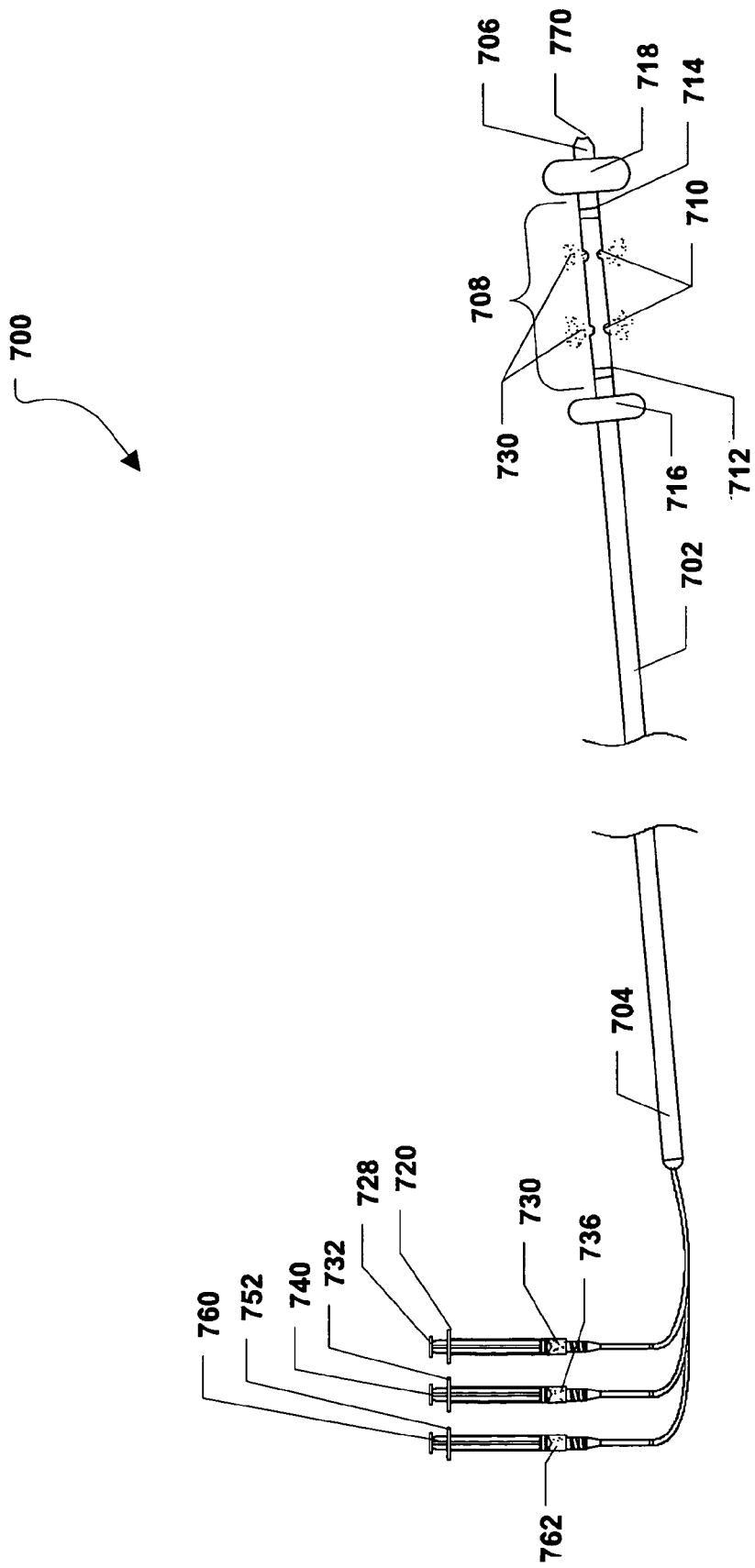
FIG. 8 is another plan view of the second embodiment of the intramedullary drug delivery device.

In a particular embodiment, when the plunger 728 of the drug delivery syringe 720 is depressed, as shown in FIG. 8, a therapeutic agent 730, described herein, can be delivered from the drug delivery syringe 720 to the drug delivery region 708 of the intramedullary drug delivery device 700 via the drug delivery tube 722. The therapeutic agent 730 can be expelled from the intramedullary drug delivery device 700 via the drug delivery fenestrations 710 within drug delivery region 708. In a particular embodiment, the therapeutic agent 730 can be one or more of the therapeutic agents described herein.

Moreover, as shown in FIG. 7, the intramedullary drug delivery device 700 can include a first balloon inflating syringe 732, which can be connected to the housing 702 via a first balloon inflating tube 734. In a particular embodiment, the first balloon inflating tube 734 can extend through the proximal end 704 of the housing 702 and can lead to the first balloon 716 of the intramedullary drug delivery device 700. The first balloon inflating syringe 732 can include a syringe housing 736. The syringe housing 736 can include a tip 738 and the first balloon inflating tube 734 can be coupled, or otherwise connected to the tip 738 of the syringe housing 736. Further, a plunger 740 can be inserted within the syringe housing 736. In alternative embodiments, the first balloon inflating syringe 732 can be removably or substantially permanently connected to the first balloon inflating tube 734, which can be removably or substantially permanently connected to the housing 702.

Figure 10:
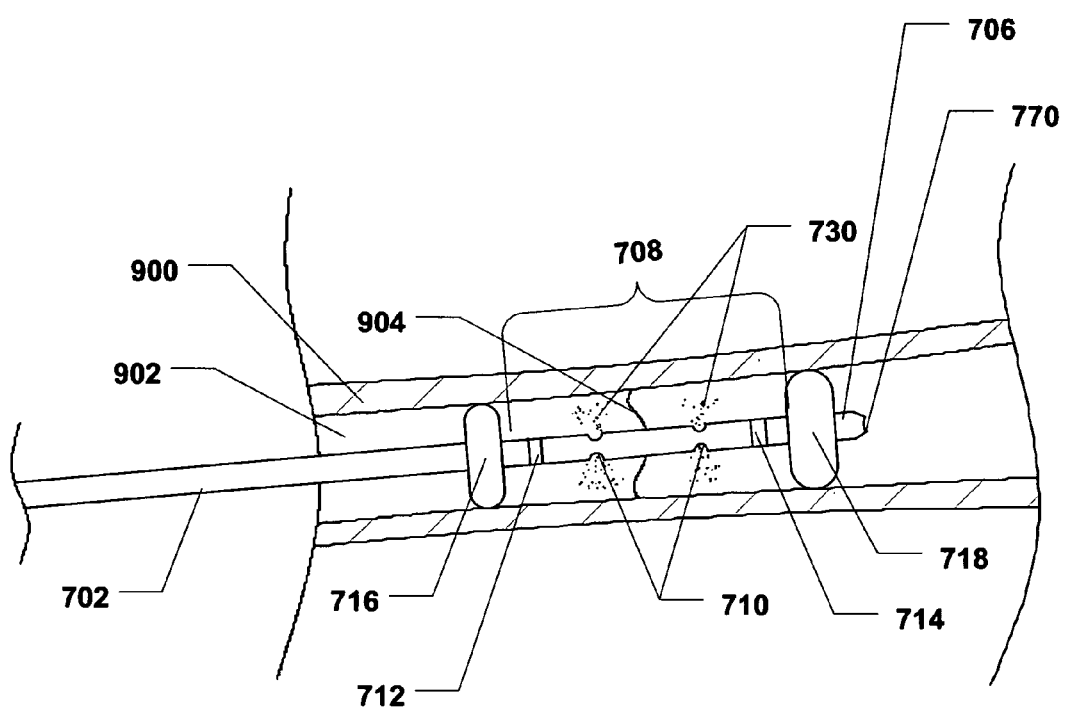
FIG. 10 is another plan view of the second embodiment of the intramedullary drug delivery device within a bone.

In a particular embodiment, when the plunger 740 of the first balloon inflating syringe 732 is depressed, an inflating fluid 742 can be delivered from the first balloon inflating syringe 732 to the first balloon 716 of the intramedullary drug delivery device 700 via the first balloon inflating tube 734. The inflating fluid 742 can inflate the first balloon 716 until the first balloon 716 engages the bone 900 as shown in FIG. 10. In a particular embodiment, the inflating fluid 742 can be air, saline, or any other biocompatible fluid.

FIG. 7 further illustrates that the intramedullary drug delivery device 700 can include a second balloon inflating syringe 752 that can be connected to the housing 702 via a second balloon inflating tube 754. In a particular embodiment, the second balloon inflating tube 754 can extend through the proximal end 704 of the housing 702 and can lead to the second balloon 718 of the intramedullary drug delivery device 700. The second balloon inflating syringe 752 can include a syringe housing 756. The syringe housing 756 can include a tip 758 and the second balloon inflating tube 754 can be coupled, or otherwise connected to the tip 758 of the syringe housing 756. Further, a plunger 760 can be inserted within the syringe housing 756. In alternative embodiments, the second balloon inflating syringe 752 can be removably or substantially permanently connected to the second balloon inflating tube 754, which can be removably or substantially permanently connected to the housing 702.

In a particular embodiment, when the plunger 760 of the second balloon inflating syringe 752 is depressed, an inflating fluid 762 can be delivered from the second balloon inflating syringe 752 to the second balloon 718 of the intramedullary drug delivery device 700 via the second balloon inflating tube 754. The inflating fluid 762 can inflate the second balloon 718 until the second balloon 718 engages the bone 900, as shown in FIG. 10. In a particular embodiment, the inflating fluid 762 can be air, saline, or any other biocompatible fluid.

In alternative embodiments, the various combinations of the drug delivery syringe 720, the drug delivery tube 722, the first balloon inflating syringe 732, the first balloon inflating tube 734, the second balloon inflating syringe 752, or the second balloon inflating tube 754 can be removably or substantially permanently connected to each other or to the housing 702.

FIG. 7 further shows that the distal end 706 of the intramedullary drug delivery device 700 can include a guide wire hole 770 that can lead to a lumen (not shown) formed within the intramedullary drug delivery device 700. As such, the intramedullary drug delivery device 700 can be inserted over a guide wire (not shown) or a guide pin (not shown). The guide wire can facilitate insertion of the intramedullary drug delivery device 700.

Figure 9:
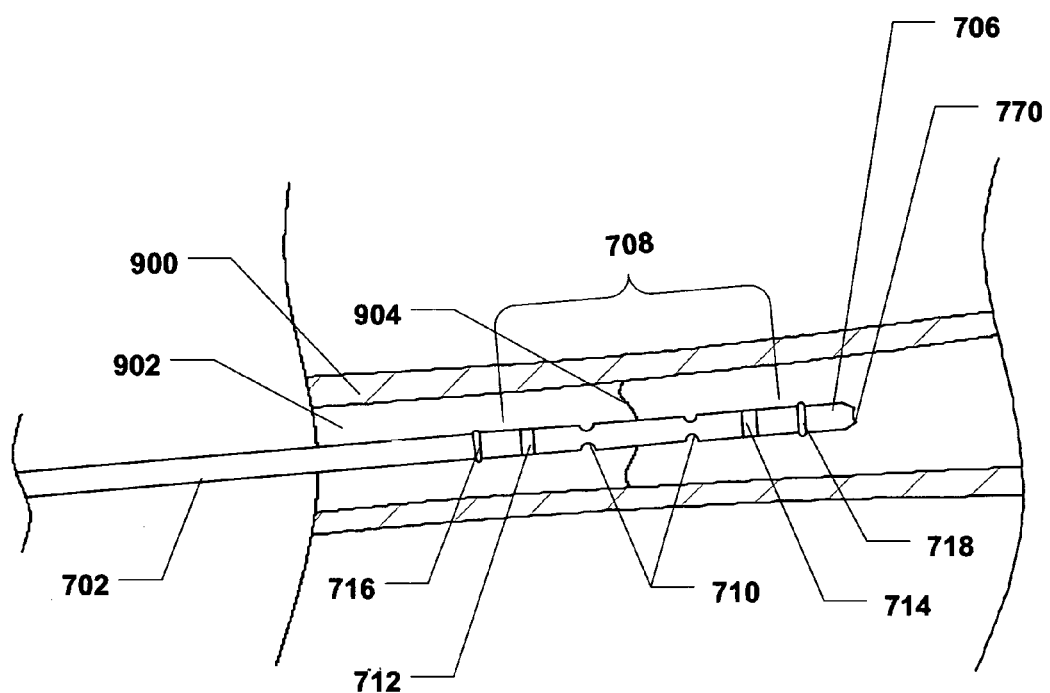
FIG. 9 is a plan view of the second embodiment of the intramedullary drug delivery device within a bone.

During use, the intramedullary drug delivery device 700 can be placed within a bone 900, as depicted in FIG. 9. In a particular embodiment, the intramedullary drug delivery device 700 can be inserted within a bone canal 902 of the bone 900. In a particular embodiment, the bone 900 can be an ulna, a radius, a humerus, a femur, a tibia, a fibula, or any other similar bone. The radiopaque markers 712, 714 can be used to properly locate the drug delivery region 708 of the intramedullary drug delivery device 700 at or near a fracture 904 within the bone 900. Specifically, in the presence of X-rays, e.g., from a fluoroscopy device, the radiopaque markers 712, 714 will be visible to allow placement of the intramedullary drug delivery device 700. In a particular embodiment, the intramedullary drug delivery device 700 can be placed so that the drug delivery region 708 spans, or otherwise straddles, the fracture 904 within the bone 900.

Additionally, as shown in FIG. 10, the balloons 716, 718 can be inflated to engage the bone 900. As such, the drug delivery region 708 can be bound by the inflated balloons 716, 718 and the balloons 716, 718 can substantially trap a therapeutic agent delivered by the intramedullary drug delivery device 700 in the area immediately adjacent to and surrounding the fracture 904.

Description of a Second Method of Treating a Bone Fracture

Figure 11:
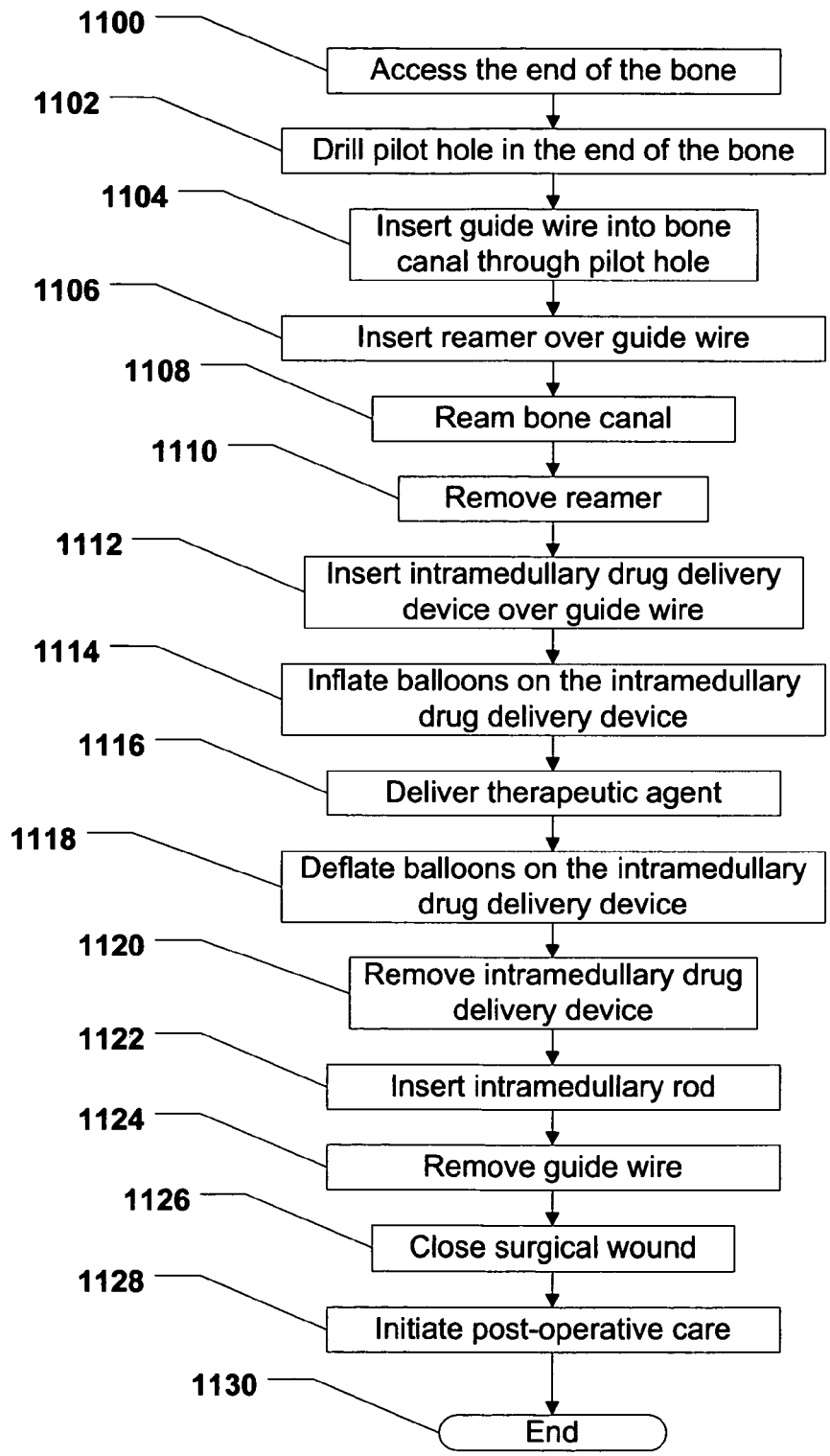
FIG. 11 is a flow chart of a second method of treating a bone fracture.

Referring to FIG. 11, a second method of treating a bone fracture is shown and commences at block 1100. At block 1100, an end of a bone can be accessed. At block 1102, a pilot hole can be drilled in the end of the bone. Moving to block 1104, a guide wire, or guide pin, can be inserted into a bone canal within the bone through the pilot hole. Thereafter, at block 1106, a bone reamer can be inserted into the bone canal over the guide wire.

Proceeding to block 1108, the bone canal can be reamed using the bone reamer. At block 1110, the bone reamer can be removed from the bone canal. Moving to block 1112, an intramedullary drug delivery device can be inserted over the guide wire. In a particular embodiment, the intramedullary drug delivery device can be an intramedullary drug delivery device according to one or more of the embodiments described herein. Further, in a particular embodiment, the intramedullary drug delivery device can be positioned within the bone so that a drug delivery region of the intramedullary drug delivery device straddles a fracture in the bone. One or more radiopaque markers on the intramedullary drug delivery device, in conjunction with an X-ray device or a fluoroscopy device, can facilitate the positioning of the intramedullary drug delivery device within the bone.

Continuing to block 1114, a pair of balloons on the intramedullary drug delivery device can be inflated. In a particular embodiment, the balloons can be inflated by depressing the plungers on a pair of balloon inflating syringes of the intramedullary drug delivery device. At block 1116, a therapeutic agent can be delivered to the bone canal. In a particular embodiment, the therapeutic agent can be delivered to the area immediately around the fracture. The balloons can help keep the therapeutic agent within the bone canal around the fracture. In a particular embodiment, the therapeutic agent can be delivered to the bone canal by depressing a plunger on a syringe of the intramedullary drug delivery device. Further, in a particular embodiment, the therapeutic agent can be bone morphogenetic protein (BMP), demineralized bone matrix (DBM), cellular material, platelet gel, or a combination thereof. Also, the therapeutic agent can include a cement, a putty, or a combination thereof, which can provide a scaffold for passive bone formation in addition to acting as a carrier for another therapeutic agent, e.g., one or more of the therapeutic agents described above.

Moving to block 1118, the pair of balloons on the intramedullary drug delivery device can be deflated. In a particular embodiment, the balloons can be deflated by retracting the plungers on the balloon inflating syringes of the intramedullary drug delivery device and withdrawing the inflation material within the balloons.

At block 1120, the intramedullary drug delivery device can be removed from the bone canal. Thereafter, at block 1122, an intramedullary rod can be inserted into the bone canal over the guide wire. At block 1124, the guide wire can be removed. Proceeding to block 1126, the surgical wound, e.g., the surgical wound used to access the end of the bone, can be closed. The surgical wound can be closed by simply allowing the patient's skin to close due to the elasticity of the skin. Alternatively, the surgical wound can be closed using sutures, surgical staples, or any other surgical technique well known in the art. At block 1128, postoperative care can be initiated. Then, the method can end at state 1130.

Conclusion

With the configuration of structure described above, the intramedullary drug delivery device provides a device that can be used to deliver a therapeutic agent to an area within a bone immediately adjacent to a fracture. One or more radiopaque markers on the intramedullary drug delivery device can be used to position a drug delivery region of the intramedullary drug delivery device immediately adjacent to the fracture. After delivery of the therapeutic agent, the intramedullary drug delivery device can be removed from the bone and an intramedullary rod or an intramedullary nail can be inserted into the bone.

In a particular embodiment, localized delivery of the therapeutic agent can be beneficial to patients that may be slow to heal, e.g., patients that smoke, diabetic patients, and patients that are taking steroids.

The above-disclosed subject matter is to be considered illustrative, and not restrictive, and the appended claims are intended to cover all such modifications, enhancements, and other embodiments that fall within the true spirit and scope of the present invention. Thus, to the maximum extent allowed by law, the scope of the present invention is to be determined by the broadest permissible interpretation of the following claims and their equivalents, and shall not be restricted or limited by the foregoing detailed description.

What is claimed is:

1. An intramedullary drug delivery device configured to be inserted within a bone canal of a bone, comprising:

a housing extending along an axis between a first axial end and a second axial end opposite the first axial end, the housing comprising an exterior surface, an interior lumen, an opening in the first axial end configured to receive a drug delivery tube and a guide wire hole in the second axial end configured to receive a guide wire;

a drug delivery tube extending through the opening such that at least a portion of the drug delivery tube is positioned within the lumen, the drug delivery tube being configured to deliver a drug into the lumen; and a drug delivery region established along the housing, the drug delivery region including a proximal end and a distal end, the proximal end includes a drug delivery fenestration and the distal end includes a drug delivery fenestration, the drug delivery fenestrations being configured to provide drug delivery from the lumen through the exterior surface of the housing, wherein the drug delivery region is configured to substantially straddle a fracture within the bone such that the drug delivery fenestration on the proximal end is positioned on one side of the fracture and the drug delivery fenestration on the distal end is positioned on another side of the fracture.

2. The intramedullary drug delivery device of claim 1, further comprising:
a first radiopaque marker on the housing; and
a second radiopaque marker on the housing and distanced from the first radiopaque marker.

3. The intramedullary drug delivery device of claim 2, wherein the drug delivery region is established between the first radiopaque marker and the second radiopaque marker.

4. The intramedullary drug delivery device of claim 1, further comprising a first balloon on the housing, the first balloon movable between a deflated position and an inflated position in which the first balloon engages the bone.

5. The intramedullary drug delivery device of claim 4, further comprising a second balloon on the housing and spaced apart from the first balloon, the second balloon movable between a deflated position and an inflated position in which the second balloon engages the bone.

6. The intramedullary drug delivery device of claim 5, wherein the first balloon, the second balloon or a combination thereof is radiopaque.

7. The intramedullary drug delivery device of claim 6, wherein the first balloon and the second balloon are radiopaque and define boundaries of the drug delivery region.

8. The intramedullary drug delivery device of claim 3, further comprising:
a first balloon disposed over the first radiopaque marker and a second balloon disposed over the second radiopaque marker.

9. The intramedullary drug delivery device of claim 1, further comprising a therapeutic agent deliverable via the drug delivery region of the housing.

10. The intramedullary drug delivery device of claim 9, wherein the therapeutic agent comprises bone morphogenetic protein (BMP), demineralized bone matrix (DBM), cellular material, platelet gel, a cement, a putty, or a combination thereof.

11. A method of treating a bone fracture, the method comprising:
inserting an intramedullary drug delivery device according to claim 1 within a bone such that a drug delivery region of the intramedullary drug delivery device straddles the fracture; and
delivering a therapeutic agent in an area surrounding the fracture.

12. The method of claim 11, wherein the inserting step further comprises moving the intramedullary drug delivery device along a guide wire.

13. The method of claim 11, further comprising:
removing the intramedullary drug delivery device from the bone.

14. The method of claim 12, further comprising: inserting an intramedullary rod within the bone.

15. A method of treating a bone fracture, the method comprising:
inserting an intramedullary drug delivery device according to claim 1 within a bone such that a drug delivery region of the intramedullary drug delivery device straddles the fracture;
inflating a first balloon and a second balloon adjacent to the drug delivery region; and
delivering a therapeutic agent in an area surrounding the fracture.

16. The method of claim 15, further comprising: deflating the first balloon.

17. The method of claim 16, further comprising: deflating the second balloon.

18. The method of claim 17, further comprising:
removing the intramedullary drug delivery device from the bone.

19. The method of claim 18, further comprising: inserting an intramedullary rod within the bone.

20. An intramedullary drug delivery device configured to be inserted within a bone canal of a bone, comprising:
a housing extending along an axis between a first axial end and a second axial end opposite the first axial end, the housing comprising an exterior surface, an opening in the first axial end and an interior lumen;
a drug delivery tube extending through the opening such that at least a portion of the drug delivery tube is positioned within the lumen, the drug delivery tube being configured to deliver a drug into the lumen;
a first radiopaque marker on the housing;
a second radiopaque marker on the housing and distanced from the first radiopaque marker;
a drug delivery region including a proximal end and a distal end, the drug delivery region being established along the housing between the first radiopaque marker and the second radiopaque marker; and
a drug delivery fenestration disposed on the proximal end and a drug delivery fenestration disposed on the distal end, the drug delivery fenestrations established in the housing within the drug delivery region configured to provide drug delivery from the lumen through the exterior surface of the housing, wherein the drug delivery region is configured to substantially straddle a fracture within the bone such that the drug delivery fenestration on the proximal end is positioned on one side of the fracture and the drug delivery fenestration on the distal end is positioned on another side of the fracture.

21. An intramedullary drug delivery device configured to be inserted within a bone canal of a bone, comprising:
a housing extending along an axis between a first axial end and a second axial end opposite the first axial end, the housing comprising an opening in the first axial end, an exterior surface and an interior lumen;
a drug delivery tube extending through the opening such that at least a portion of the drug delivery tube is positioned within the lumen, the drug delivery tube being configured to deliver a drug into the lumen;
a first radiopaque marker on the housing;

a second radiopaque marker on the housing and distanced from the first radiopaque marker;

a drug delivery region including a proximal end and a distal end, the drug delivery region being, the drug delivery fenestrations established along the housing between the first radiopaque marker and the second radiopaque marker, the drug delivery region including a drug delivery fenestration disposed on the proximal end and a drug delivery fenestration disposed on the distal end, configured to provide drug delivery from the lumen through the exterior surface of the housing, wherein the drug delivery region is configured to substantially straddle a fracture within the bone such that the drug delivery fenestration on the proximal end is positioned on one side of the fracture and the drug delivery fenestration on the distal end is positioned on another side of the fracture;

a first balloon adjacent to the drug delivery region; and a second balloon adjacent to the drug delivery region.

22. An intramedullary drug delivery device configured to be inserted within a bone canal of a bone, comprising:

a housing extending along an axis between a first axial end and a second axial end opposite the first axial end, the housing comprising an opening in the first axial end, an exterior surface and an interior lumen;

a drug delivery tube extending through the first opening such that at least a portion of the drug delivery tube is positioned within the lumen, the drug delivery tube being configured to deliver a therapeutic agent into the lumen;

a drug delivery region including a proximal end and a distal end, the drug delivery region being configured to substantially straddle a fracture within the bone, the drug delivery region including a drug delivery fenestration disposed on the proximal end and a drug delivery fenestration disposed on the distal end, configured to provide drug delivery from the lumen through the exterior surface of the housing;

a therapeutic agent deliverable to an area substantially near the fracture via the drug delivery region; and a balloon on the housing and movable between a deflated position and an inflated position.

23. A kit for treating a fracture within a bone, the kit comprising:

an intramedullary drug delivery device configured to be inserted within the bone and comprising a housing extending along an axis between a first axial end and a second axial end opposite the first axial end, the housing comprising an opening in the first axial end, an exterior surface and an interior lumen, the drug delivery device comprising a drug delivery tube extending through the first opening such that at least a portion of the drug delivery tube is positioned within the lumen, the drug delivery tube being configured to deliver a therapeutic agent into the lumen, the drug delivery device further comprising a drug delivery region including a proximal end and a distal end, the drug delivery region being configured to substantially straddle the fracture, the drug delivery region including a drug delivery fenestration disposed on the proximal end and a drug delivery fenestration disposed on the distal end, configured to provide drug delivery from the lumen through the exterior surface of the housing, wherein the drug delivery fenestration on the proximal end is positioned on one side of the fracture and the drug delivery fenestration on the distal end is positioned on another side of the fracture;

a therapeutic agent deliverable to an area within the bone substantially near the fracture via the drug delivery region;

an intramedullary rod configured to be installed within the bone; and a balloon on the housing and movable between a deflated position and an inflated position.

24. The intramedullary drug delivery device of claim 21, further comprising at least one balloon inflating tube extending through the opening in communication with at least one of the first balloon and the second balloon, the at least one balloon inflating tube being configured to deliver a material to at least one of the first balloon and the second balloon to move at least one of the first balloon and the second balloon between a deflated position and an inflated position.

25. The intramedullary drug delivery device of claim 21, further comprising first and second balloon inflating tubes each extending through the opening, the first balloon inflating tube being in communication with the first balloon and the second balloon inflating tube being in communication with the second balloon, the first balloon inflating tube being configured to deliver a material to the first balloon to move the first balloon between a deflated position and an inflated position and the second balloon inflating tube being configured to deliver a material to the second balloon to move the second balloon between a deflated position and an inflated position.

26. The intramedullary drug delivery device of claim 22, further comprising a balloon inflating tube extending through the opening in communication with the balloon, the balloon inflating tube being configured to deliver a material to the balloon to move the first balloon between the deflated position and the inflated position.

* * * * *